US00PP32134P2

(12) United States Plant Patent
Hansen

(10) Patent No.: US PP32,134 P2
(45) Date of Patent: Aug. 25, 2020

(54) ***HEUCHERA* PLANT NAMED 'TIMELESS NIGHT'**

(50) Latin Name: ***Heuchera* hybrid**
Varietal Denomination: Timeless Night

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/501,324

(22) Filed: Mar. 26, 2019

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 5/02
See application file for complete search history.

*Primary Examiner* — Kent L Bell

(57) ABSTRACT

The new and distinct hybrid of *Heuchera* plant named 'Timeless Night' with small to medium-sized, shallowly-lobed, glossy, greyed-purple leaves with rounded apices and lobes. Numerous, moderately-branched, upright, dark-purple flower stems are repeatedly produced from early summer to early fall for about fourteen weeks displaying small, rosy-pink flowers starting just above the foliage. The habit of the new plant is compact, herbaceous perennial with mounds of leaves. It is vigorous and produces showy flowers over a long season, effective as a specimen plant, en masse in the landscape, or as a container plant.

2 Drawing Sheets

Botanical denomination: *Heuchera* hybrid.
Variety denomination: 'Timeless Night'.

STATEMENT REGARDING PRIOR DISCLOSURES UNDER 37 CFR 1.77(B)(6)

The first public disclosure of the claimed plant, was a non-enabling brief description and photograph on a website and email release to customers, made by Walters Gardens, Inc. on Feb. 1, 2019. The first public sales of *Heuchera* 'Timeless Treasure' was by Walters Gardens, Inc. on Jun. 19, 2018. Walters Gardens, Inc. obtained the new plant and information about the new plant directly from the inventor. No plants of *Heuchera* 'Timeless Night' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of *Heuchera* 'Timeless Night'. 'Timeless Night' was hybridized by the inventor on Jan. 27, 2015 at a wholesale perennial nursery in Zeeland, Mich., USA. The seed or female parent was 'Berry Timeless' U.S. Plant Pat. No. 26,357 and the pollen or male parent was a proprietary unreleased hybrid known as 13-700-1 (not patented).

*Heuchera* 'Timeless Night' was first selected in the fall of 2016 and passed final evaluation in the fall of 2017 from among many other seedlings from the same cross and hundreds of other crosses and assigned the breeder code 15-11-1 through the remaining evaluation process. *Heuchera* 'Timeless Night' has been asexually propagated initially by basal cuttings at the same nursery in Zeeland, Mich. in 2016 and later by sterile, shoot-tip, tissue culture propagation, and the resultant plants have remained stable and continued to exhibit the same characteristics as the original plant for multiple generations.

BRIEF SUMMARY OF THE INVENTION

The nearest comparison varieties include: 'Black Pearl' U.S. Plant Pat. No. 29,395, 'Timeless Treasure' U.S. Plant patent application Ser. No. 16/350,856, 'Timeless Glow' U.S. Plant patent application Ser. No. 16/350,865, 'Grape Timeless' U.S. Plant patent application Ser. No. 16/350,864, 'Obsidian' U.S. Plant Pat. No. 14,836, 'Blackout' U.S. Plant Pat. No. 20,613 and 'Black Beauty' U.S. Plant Pat. No. 13,288. 'Black Pearl' has larger, more sinuate foliage, and the flower stems taller, fewer with a much shorter flowering period and flowers are more cream-colored. 'Timeless Treasure' has similar flowering period, but the flowers are lighter pink and more outwardly facing and the foliage has a heavy silvering between the veins. 'Timeless Glow' has pinkish flowers on much shorter stalks with fewer flowers per stalk and the foliage color is chartreuse with more rounded lobes. 'Grape Timeless' has similar habit, leaf size and long flowering period but the flowers are more spaced and the foliage is purple without silvering between the veins. 'Obsidian' has smaller flowers of creamy-chartreuse over a much shorter period and the foliage is more mahogany and lighter than the new plant. 'Blackout' has lighter brownish-purple in the foliage and the flowers are smaller and creamy white. 'Black Beauty' has shorter unbranched peduncles with fewer cream-colored flowers, and the top foliage surface color is a darker blend of greyed-purple. The female parent, 'Berry Timeless', has a similar profusion of flowers throughout the season but the flower color is lighter pink and the foliage is light green with slight silvering between the veins. The male parent has larger foliage with greyed-purple color and the flowers are cream-colored on taller stems.

*Heuchera* 'Timeless Night' differs from its parents as well as all other coral bells known to the applicant in the following combined traits:

1. The small to medium-sized, flat, glossy foliage has rounded apices and lobes;
2. Leaf blades emerge purplish-red and develop a glossy, dark, greyish-purple with maturity, without developing a silver overlay between veins;
3. Leaf blades are shallowly dissected with apices rounded and muconulate.
4. Flowers are small, outwardly-facing to slightly drooping, rosy-pink on dark-purple stems.
5. Flowering period begins in early summer and continues for about fourteen weeks into early fall with repeat panicles.
6. Compact, short, moderately-branched, dark-purple panicles display flowers at multiple nodes beginning just above the foliage.
7. The new plant is vigorous and produces compact clumps and many small to medium-sized individual leaves.

BRIEF DESCRIPTION OF THE DRAWINGS

The photographs of *Heuchera* 'Timeless Night' demonstrate the overall appearance of the plant including the unique traits of a plant in a shaded trial block and partially shaded greenhouse in Zeeland, Mich. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
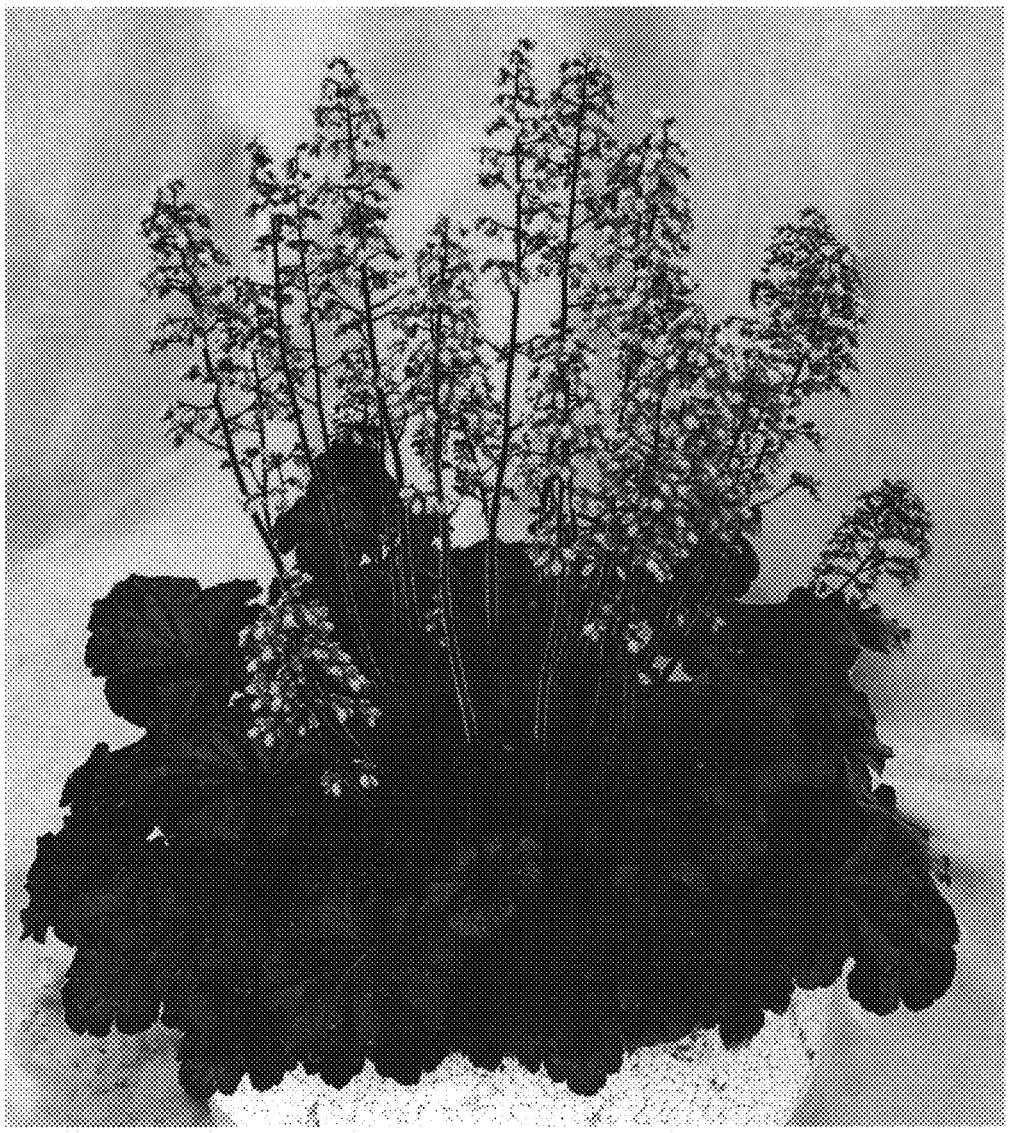
FIG. 1 shows a two-year-old plant grown in a container in a partially shaded greenhouse in peak flowering season.
Figure 2:
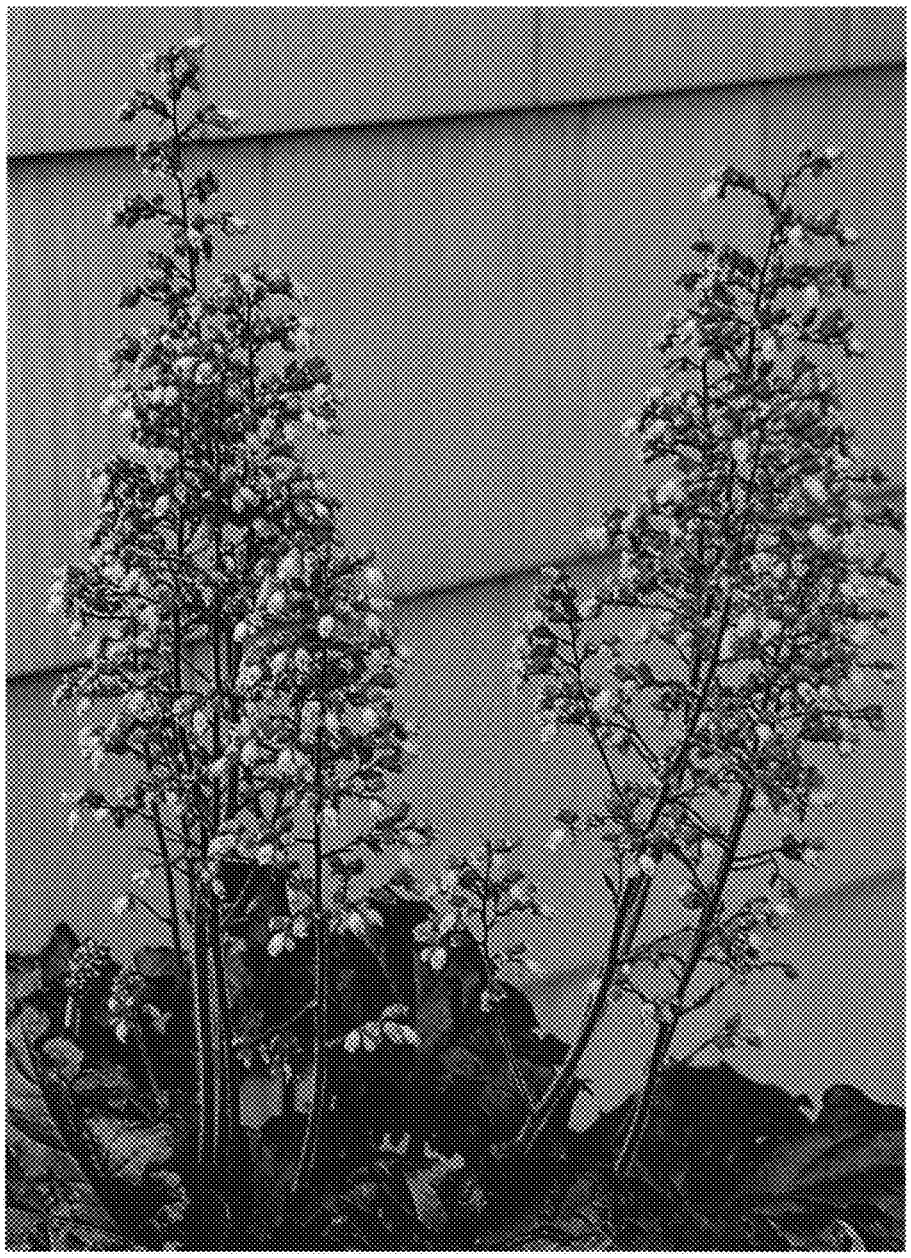
FIG. 2 shows a close-up of flower panicles with buds and flowers from a two-year-old plant.

The following description is based on two-year-old plants growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 'Berry Timeless'; the male or pollen parent was the proprietary unreleased hybrid known only by the breeder code 13-700-1, a selection from the crosses consisting of 'Fire Chief' U.S. Plant Pat. No. 21,880, 'Hercules' (not patented), 'Cherry Cola' U.S. Plant Pat. No. 22,967 and a proprietary selection of the seed cultivar 'Dark Mystery' (not patented);

Plant habit: Hardy herbaceous perennial with basal rosette of foliage; mounded foliage about 21.5 cm tall and 42.0 cm in diameter with scapes to about 65.0 cm long; with about 12 stems per plant to about 2.0 cm long and 1.0 cm diameter at base, with about 8 to 10 leaves per stem; about 40 scapes during peak flowering;

Roots: Fibrous, finely branched; color nearest RHS 155D on young roots and nearest RHS 159D on mature roots;

Growth rate: Rapid, rooting from cutting in two weeks and finishing in three-liter container in about two and a half months;

Foliage: Cordate to nearly rounded; micro-puberulent adaxial and abaxial; palmately shallowly lobed with five main lobes shallowly dissected, less than one-quarter of the distance to the petiole; apex and lobe apices rounded and mucronulate; base cordate with basal lobes nearly overlapping to overlapping about 0.5 cm; margins crenate to mucronulate, ciliolate; lustrous adaxial and abaxial; held nearly horizontal; margin slightly undulate;

Leaf blade size: To about 12.5 cm wide and 12.8 cm long, average about 9.5 cm wide and 10.2 cm long;

Leaf color: Spring and young emerging adaxial nearest RHS N186C; spring young emerging abaxial nearest RHS 187B; mature mid-season adaxial nearest blend between RHS N186A and RHS 202A without silver overlay; abaxial mature mid-season nearest blend of RHS N79A and RHS N186C; over-wintered adaxial nearest blend between RHS N198B and N186A; abaxial over-wintered between RHS N186C and RHS N186B;

Leaf quantity: About 100 per plant;

Veins: Palmate; sparsely hirsutulous and costate abaxial, glabrous and nearly flat adaxial;

Vein color: Emerging or early spring adaxial nearest RHS N186D and abaxial nearest RHS N186D; mid-season flowering adaxial proximally blend of nearest RHS 182B and RHS N187B distally becoming same as surrounding leaf, mid flowering season abaxial nearest RHS 187B; late season adaxial same as mid-season, abaxial nearest RHS N186D;

Petiole: Cylindrical, base amplexicaul; pubescent with hairs to 1.2 mm long; to about 18.0 cm long and 3.0 mm wide above stipule; average about 14.0 cm long and about 2.5 mm diameter above stipule;

Petiole color: Emerging leaf nearest RHS N186D; flowering season mature leaf nearest RHS N186C; late season nearest RHS N186C;

Stipule: Flared at base of petiole; glaucous abaxial and adaxial; margin ciliate; to about 2.2 cm long and about 12.0 mm wide at base; with two lateral projections of about 5.0 mm long and 2.0 mm across in distal portion;

Stipule color: Young expanding adaxial and abaxial between RHS 64A and RHS 64B; mature adaxial and abaxial nearest 64A; overwintered between RHS NI86C and RHS N186D;

Peduncle: Panicle; cylindrical; stiff; pubescent; upright; moderately-dense, compound branched; to about 65.0 cm long and 5.0 mm diameter at base, average about 54.0 cm tall and 4.0 mm diameter; about 40 per plant with up to about 800 flowers per panicle, average about 600; initial flowers just above foliage; moderately-branched panicle with up to 28 branches up to 18.5 cm long and 1.5 mm diameter decreasing distally, average 21 branches per panicle; lowest two to four branches compound with main branch upwardly, distal branches upwardly to outwardly, arching and curving downward; branches subtended by single foliar bract; flower density moderate;

Peduncle color: Young expanding nearest RHS N186C, mature nearest RHS N186B;

Foliar bract: Proximal bracts cordate, to 8.5 cm long and 9.0 cm across, truncate base, acute apex and lobes, margin mucronulate and ciliolate, lobes moderately incised to near half way to petiole, petiole to 6.5 cm long and 2.5 mm across at base; distal bracts decreasing in length and width, becoming more oblong palmate to lanceolate; incised margins to deeply lobed, apex acute, truncate clasping base, sessile, decreasing to 4.0 mm long and 1.5 mm across;

Foliar bract color: Same as leaves;

Flowering longevity: Panicle effective for about two to four weeks; individual flowers effective about 4 days; self-cleaning;

Flowering period: Beginning early summer and repeating with new panicles without the need to remove old panicles through early fall for about 14 weeks;

Pedicel: Cylindrical; puberulent; to about 2.0 mm long and 0.5 mm diameter, average about 1.5 mm long and 0.5 mm diameter; attitude outwardly to slightly drooping;

Pedicel color: Nearest RHS 187C;

Buds one day prior to opening: Ellipsoidal; rounded apex and attenuate base; puberulent to glandular; about 3.5 mm long and 2.5 mm diameter;

Bud color one day prior to opening: Between RHS 58D and RHS 59C;

Flower: Perfect; campanulate; actinomorphic; about 6.0 mm long and 4.0 mm in diameter at corolla face;

Flower attitude: Outwardly to slightly drooping;

Calyx: Base fused in proximal 2.5 mm to form hypanthium; puberulent to glandular abaxial, glabrous adaxial; about 4.5 mm long and 3.5 mm wide at apex;

Sepals: Five; lanceolate; acute apex, fused in basal 2.5 mm; to about 4.5 mm long and 1.5 ram wide at fusion;

Sepal color: Abaxial apical 0.5 mm nearest RHS 59A and proximal 3.0 mm nearest RHS 59D, adaxial apical 0.5 mm nearest RHS 59A and proximal 3.0 mm nearest RHS 59D;

Petals: Five; oblanceolate to spatulate; acute apex and attenuate base; margin entire; glabrous adaxial and abaxial; about 2.5 mm long and 1.0 mm wide in middle;

Petal color: Abaxial and adaxial nearest RHS 63C;

Androecium: Five; adnate to adaxial sepal about 1.0 mm above base;

*Filaments*.—Five; thin; cylindrical; glabrous; about 2.0 mm long and about 0.3 mm diameter; color nearest RHS NN155C distally and nearest RHS 65D proximally.

*Anthers*.—Ellipsoidal, distinct, basifixed, longitudinal; about 0.7 mm long and about 0.5 mm across; color nearest RHS N170A.

*Pollen*.—Moderately abundant, color nearest 4C.

Gynoecium: One, two-beaked; half-inferior; bifid style with pistil split at ovary; about 5.2 mm long;

*Style*.—Bifid; split apart at apex of ovary; about 4.0 mm long and about 0.5 mm diameter; color nearest RHS N155C distally and nearest RHS 62D proximally.

*Stigma*.—Globose apex, about 0.2 mm diameter; color nearest RHS NN155C.

*Ovary*.—Half-inferior, about 1.0 mm long and. 2.0 mm diameter; ellipsoidal to globose; acute apex and base rounded; color nearest RHS N170D.

Fruit: Not yet observed;

Seeds: Not yet observed;

Disease and pest tolerance: The new plant grows best with ample moisture and drainage in either part sun or full shade. Cold hardy from USDA zones 4 to 9. Other resistance and tolerance outside of that normal for *Heuchera* is not known.

It is claimed:

1. The new and distinct Coral Bells plant named *Heuchera* 'Timeless Night' as herein described and illustrated.

* * * * *